(12) United States Patent
Egger et al.

(10) Patent No.: US 7,970,719 B2
(45) Date of Patent: Jun. 28, 2011

(54) METHOD AND SIMULATION DEVICE FOR STRUCTURALLY INDIVIDUALIZED SIMULATION OF THE INTRODUCTION OF A WALL SUPPORT ELEMENT INTO A SECTION OF A TUBULAR STRUCTURE

(75) Inventors: Jan Egger, Limburg (DE); Bernd Freisleben, Marburg (DE); Stefan Grosskopf, Nürnberg (DE); Carlos Leber, Limburg (DE)

(73) Assignee: Siemens Aktiengesellschaft, Munich (DE)

( * ) Notice: Subject to any disclaimer, the term of this patent is extended or adjusted under 35 U.S.C. 154(b) by 197 days.

(21) Appl. No.: 12/457,281

(22) Filed: Jun. 5, 2009

(65) Prior Publication Data

US 2009/0304245 A1 Dec. 10, 2009

(30) Foreign Application Priority Data

Jun. 6, 2008 (EP) .................................... 08010365
Jun. 6, 2008 (EP) .................................... 08010366

(51) Int. Cl.
*G06N 5/00* (2006.01)
(52) U.S. Cl. ........................................... 706/44; 706/45
(58) Field of Classification Search .................... 706/44, 706/45; 382/128
See application file for complete search history.

(56) References Cited

FOREIGN PATENT DOCUMENTS

| DE | 102006058908 A1 | 4/2008 |
|---|---|---|
| DE | 102007039207 A1 | 2/2009 |

OTHER PUBLICATIONS

Hernandez-Hoyos, et al., Computer-assisted Analysis of Three-dimensional MR Angiograms, RadioGraphics, Mar. 22, 2002, pp. 421-436.*
"Pre-Operative Simulation of Tubular Prosthesis and Y-Stents for Endovascular Treatment of Stenosis and Aneurysms." English Abstract for previously submitted Reference No. 14, entitled "Präoperative Simulation von Rohrprothesen und Y-Stents zur endovaskulären Behandlung von Stenosen und Aneurysmen," Mar. 2007.
American Heart Association. "Carotid Artery Stenosis." 2009.

(Continued)

*Primary Examiner* — Wilbert L Starks, Jr.
(74) *Attorney, Agent, or Firm* — Harness, Dickey & Pierce, P.L.C.

(57) ABSTRACT

A method is described for structurally individualized simulation of the introduction of a wall support element into a section of a tubular structure. To this end, image data of the interior of the section of the tubular structure are provided. A start point and an end point of the section of the tubular structure are then determined, and a lumen and a profile line of the tubular structure are determined between the start point and the end point. Furthermore, an individual elastic structure model for the section of the tubular structure is identified by adapting a tubular elastic initial model to the section of the tubular structure on the basis of the identified lumen and the profile line, and a tubular elastic wall support element model which is positioned inside the individual structure model is provided. In at least one embodiment, the wall support element model is then virtually expanded stepwise, a check for collisions between the wall support element model and the individual structure model being carried out in each expansion step. At the positions where a collision is identified, the wall support element model and the individual structure model are modified at least locally while taking into account the elasticity of the individual structure model. A method for driving an image display device, by using such a simulation method, and a simulation device are furthermore described.

20 Claims, 12 Drawing Sheets

OTHER PUBLICATIONS

Penn State Milton S. Hershey Medical Center. "A to Z topics—Carotid Artery Stenosis and Stroke." 2004.
Boskamp, Tobias et al.; New Vessels Analysis Tool for Morphometric Quantification and Visualization of Vessels in CT ans MR Imaging Data Sets; RadioGraphics, vol. 24, No. 1, Seiten 287-297; Published Online; Others; 2004.
M. Kass, A. Witkin, D. Terzopoulos; Snakes: Active Contour Models, International Journal of Computer Vision, 321-331 (1988), 1987 Kluwer Academic Publishers, Boston, Manufactured in the Netherlands; Publikation "A Note on Two Problems in Connexion with Graphs", Numerische Mathematik 1, Seiten 269-271, 1959; Others.
J.Egger et al., "Fast self-collision detection and simulation of bifurcated stents to treat abdominal aortic aneurysms (AAA)", 29th Annual Int. Conf. of the IEEE Engin. in Medicine and Biology Society, Lyon, Frankreich, IEEE Press; 6231-6234, Aug. 2007; Others.
Egger J. et al., "Preoperative Measurement of Aneurysms and Stenosis and Stent-Simulation for Endovascular Treatment", IEEE Int. Symposium on Biomedical Imaging: From Nano to Macro, Washington (D.C.), USA, IEEE Press; 392-395, Apr. 2007; Others.
Henry Yen-Chin Huang, "Theoretical and Experimental Modelling of Stress within the Neck of Endoluminal Grafted Artery", Dissertation (2006); Others.
M.Kass,A.Witkin and D.Terzopoulos, "Constraints on Deformable Models: Recovering 3D Shape and Nongrid Motion", Artificial Intelligence, 36:91-123,1988; Others.

Egger J. et al., "Präoperative Simulation von Rohrprothesen und Y-Stents zur endovaskulären Behandlung von Stenosen und Aneurysmen", Bildverarbeitung für die Medizin, München, Springer-Verlag; 182-186, März 2007; Others.
Q.J. Durward et al., "Carotid Endarterectomy in Nonagenarians", Arch Surg., 140:625-628,2005; Others.
W.Hacke, "Stent-Protected Percutaneous Angioplasty of the Carotid Artery vs. Endarterectomy", Presented at the European Stroke Conference, Brussels, May 2006; Others.
J.S.Yadav et al., "Stenting and Angioplasty with Protection in Patients at High Risk for Endarterectomy Investigators. Protected Carotid-Artery Stenting versus Endarterectomy in High Risk Patients", N. Engl J Med, 351:1493-1501, 2004; Others.
S.M.Kim et al., "Finite Element Analysis of Stent Expansion Considering Stent, Artery and Plaque Interaction", Proc. of the 24th IASTED int Conf. on Biomed. Engineering, 143-146,2006; Others.
J.J. Vitek, "Technique of Carotid Angioplasty with Stenting", Russian Neurosurgery—Scientific-Practical Journal of Russia Neurosurgical Association., vol. 2 (2), 2000; Others.
T.Möller et al., "Fast, Minimum Storage Ray/Triangle Intersection", Journal of Graphics Tools, 2(1): 21-28, 1997; Others.
Klinikum der Univ. München-Großhadern. Neurochirurgische Klinik und Poliklinik, Spezialbereiche/Neurovaskulär/Gefäßstenosen/Verschlüsse, "Karotisstenose" May 5, 2009; Others.

* cited by examiner

METHOD AND SIMULATION DEVICE FOR STRUCTURALLY INDIVIDUALIZED SIMULATION OF THE INTRODUCTION OF A WALL SUPPORT ELEMENT INTO A SECTION OF A TUBULAR STRUCTURE

PRIORITY STATEMENT

The present application hereby claims priority under 35 U.S.C. §119 on European patent application numbers EP08010366 filed Jun. 6, 2008 and EP08010365 filed Jun. 6, 2008, the entire contents of each of which are hereby incorporated herein by reference.

FIELD

At least one embodiment of the invention generally relates to a method and/or a simulation device for structurally individualized simulation of the introduction of a wall support element into a section of a tubular, i.e. pipe or hose-shaped structure. At least one embodiment of the invention furthermore generally relates to a method for driving an image display device for displaying image data of the interior of a tubular structure, the simulation being used, as well as to a computer program product with which the method according to at least one embodiment of the invention can be carried out.

BACKGROUND

A typical case in which a wall support element is introduced into a section of a tubular structure lies in the medical field, when blood vessels constricted by stenoses need to be kept open with the aid of a so-called "stent", i.e. a vascular prosthesis, or when they need to be lined in the event of an aneurysm in order to prevent the aneurysm from bursting. In this context, FIG. 1 shows the treatment of a carotid stenosis as an example. A carotid stenosis is a constriction of the carotid artery supplying the brain. It occurs owing to pathological modifications of the vessel wall, often connected with hardening. In the scope of an endovascular treatment of such a stenosis, a catheter K is initially guided into the vessel G as far as the lesion L, i.e. as far as the constriction (see FIG. 1, left). A folded stent S is then brought to the constriction by means of the catheter K (see FIG. 1, middle) and expanded there. The expansion presses the thickened sites outward as far as possible, so that an acceptable diameter is again achieved in the interior of the vessel G (see FIG. 1, right).

In order to select the appropriate stent for the individual case in question, before fitting the stent it would be expedient to carry out a simulation which is adapted as far as possible to the current situation, i.e. the vessel in question and the size and nature of the lesion. Methods for simulating the placement of stents in blood vessels are described, for example, in DE 10 2006 058 908 A1 and DE 10 2007 039 207 A1. A wireframe model of a stent is fitted virtually into the vessel, the model of the vessel structure having been generated with the aid of image data from an imaging method, for example with a magnetic resonance tomograph or a computer tomograph. The model of the vessel structure is rigid in this simulation method. Precisely in the case of a stent simulation, however, it is expedient to be able to simulate the behavior of highly coiled vessels which can be smoothed by placement of the stent. In this way, the stent dimensions of the selected stent can be assessed better in advance even in such complicated cases. To this end, it is helpful when the behavior or deformation of the vessel wall can also be taken into account in the simulation.

The publication "Finite Element Analysis of Stent Expansion Considering Stent, Artery and Plaque Interaction" by S. M. Kim and S. Y. Park in Proceedings of the 24th IASTED International Conference on Biomedical Engineering, 143-146, 2006, describes a simulation method in which the interaction between the stent and the artery, as well as the plaque, are analyzed with the aid of a finite element method. In the method described there, very elaborate reconstructed models of the stent and the arteries are required. Furthermore, the dissertation by H. Y.-C. Huang, "Theoretical and Experimental Modelling of Stress within the Neck of Endoluminal Grafted Artery", University of New South Wales, 2006, describes a way of compiling an elastic vessel model and thereby modeling the stent/vessel wall interaction during a stent expansion in the scope of a finite element method. Here, nonlinear mathematical models are developed for different arteries. The development of the models is likewise extraordinarily time-consuming, more than one day of computer time sometimes being required for one model.

The methods mentioned above are therefore very useful, for example for developing new stents or checking already existing stents. For patient-specific simulation in situ before introducing a stent, for example to assist in the selection of a stent suitable for the current case, these methods are however unsuitable owing to the time they take.

SUMMARY

In at least one embodiment of the present invention, a method and a suitable simulation device are provided for structurally individualized simulation of the introduction of a wall support element into a section of a tubular structure, with which the behavior of the wall structure can also be simulated sufficiently well in a relatively short time.

The method according to at least one embodiment of the invention comprises the following method steps:

a) First, preferably three-dimensional image data are provided which comprise at least image data of the interior of the section of the tubular structure. This may for example involve suitable magnetic resonance tomography recordings, computer tomography recordings, PET or SPECT images, etc. Here, it is particularly preferable to use a method in which the detailed contours of the tubular structures can be seen particularly well. For example, a contrast agent recording may be recommendable for a vessel study.

b) A start point and an end point are then set inside the section of the tubular structure. This may for example be done by an operator via a suitable user interface in the displayed image data of the section of the tubular structure.

c) In addition, the lumen of the section of the tubular structure between the start point and the end point is determined on the basis of the image data.

d) A profile line, preferably the so-called "centerline", of the section of the tubular structure between the start and end points is furthermore determined. The determination of the lumen of the relevant section of the tubular structure, and of the profile line, may be carried out with different known methods which are moreover used for determination of centerlines or for the segmentation of vessels etc. for other tasks.

e) This is followed by identification of an individual or individualized elastic structure model for the section of the tubular structure. To this end, according to at least one embodiment of the invention, a tubular elastic initial model is adapted to the section of the tubular structure on the basis of the identified lumen and the profile line of the tubular structure.

f) A tubular elastic wall support element model, which is positioned inside the individual structure model, is furthermore provided. To this end, the wall support element model should preferably have an initial maximum diameter which is less than a minimum diameter of the elastic structure model adapted to the lumen.

The wall support element model may, for example, be provided by selection from existing models which are stored in a memory, and to which for example an operator has access via a user interface. Virtual positioning of the wall support element model inside the individual structure model may also be carried out with the aid of the user interface.

In another embodiment of the method, the wall support element model is constructed in the scope of the simulation method, preferably by using the profile line.

Particularly preferably, the individual structure model is fitted into the structure model so that the centerline of the wall support element model extends coaxially with the profile line of the structure model.

g) Lastly stepwise virtual expansion of the wall support element model is carried out, in a similar way as a stent is actually deployed in reality by way of a balloon catheter or the like. According to at least one embodiment of the invention, a check for collisions between the wall support element model and the individual structure model is carried out in each expansion step. At least at the positions where a collision is identified, the wall support element model and the individual structure model are modified at least locally while taking into account the elasticity of the individual structure model, i.e. by using the parameters specifying the elasticity of the structure model.

Initial uses have shown that this method works extraordinarily rapidly in comparison with previously known methods, and therefore that a very accurate individual simulation of the placement of a stent in an artery as possible. The individual conditions for the use in question can be predicted with high accuracy by using the electronic elastic structure model. The special type of construction of the individual elastic structure model by way of adapting a simple initial model can be carried out without great computer outlay and therefore particularly rapidly. Since, apart from the positioning, the initial model does not need to be individual, standardized initial models with different starting sizes for different vessel types can therefore be used substantially independently of the individual vessel.

At least one embodiment of the method is therefore particularly suitable for use immediately before an intervention, for example in order to use the simulation results besides other parameters for the selection of a suitable stent. It is, however, specifically to be pointed out that the method is not restricted to this application, even though it will preferably be used in the medical field to simulate the placement of stents in vessels or other tubular structures. In principle, the method may be used whenever any tubular structure needs to be reinforced by a wall support element, for example so that defective hose sites in an engineering system, which are not readily replaceable, can be made fit for use again at least temporarily with the aid of a stent-like wall support element.

The simulation device according to at least one embodiment of the invention for carrying out the method according to the invention comprises the following components:

a) An image data interface for receiving image data which comprise at least image data of the interior of the section of the tubular structure.

b) A position determination unit for determining a start point and an end point of the section of the tubular structure. This may be a unit which comprises a suitable user interface or interacts therewith in a suitable way, so that an operator can establish the start and end points, for example in the image data of the tubular structure.

c) A lumen determination unit for determining a lumen of the section of the tubular structure between the start point and the end point on the basis of the image data.

d) A profile line determination unit for determining a profile line between the start point and the end point on the basis of the image data.

e) A structure model identification unit for identifying an individual elastic structure model for the section of the tubular structure by adapting a tubular elastic initial model to the section of the tubular structure on the basis of the identified lumen and the profile line.

f) A wall support element model identification unit providing a tubular elastic wall support element model which is positioned inside the individual structure model.

For example, this may be a user interface which is designed so that an operator can select a suitable wall support element model from a memory in which various wall support element models are stored, and for example position it virtually via a graphical user interface, or assist automatic positioning.

It may however also be a unit which is for example already capable from the previously identified data, for example the identified lumen, the profile line and other data about the vessel and/or the lesion, of automatically constructing or selecting a suitable wall support element with particular parameters, or at least making a preselection and displaying it to the operator for them to confirm or modify the automatic selection.

g) An expansion unit for stepwise virtual expansion of the wall support element model, a check for collisions between the wall support element model and the individual structure model being carried out in each expansion step, and the wall support element model and the individual structure model being modified at least locally at the positions where a collision is identified, while taking into account the elasticity of the individual structure model.

A multiplicity of the components of the simulation device may be embodied in the form of software modules on a suitable computer unit, for example on a control computer of the imaging system with which the image data are identified, or on a diagnostic station which can access the image data via a suitable image data interface. An embodiment which is produced as far as possible in the form of software modules has the advantage that pre-existing imaging systems, diagnostic stations or the like can be retrofitted more easily in order to function according to the invention. It is then expedient, for example, for a suitable graphical user interface to be available which can be used jointly by the individual software components, for example by the position determination unit, the wall support element model identification unit and the positioning unit.

The dependent claims and the rest of the description respectively contain particularly advantageous refinements and configurations of embodiments of the invention; the simulation device according to at least one embodiment of the invention may also be refined according to the dependent claims.

In the method according to at least one embodiment of the invention, a simple tubular elastic initial model is adapted to the identified lumen of the tubular structure, so as to generate an individual elastic structure model. This may, for example, be done by using a cylindrical initial model which is arbitrarily deformable along the cylinder axis. This initial model may be placed so that the cylinder axis extends exactly along the profile line of the relevant section of the tubular structure. The initial model is subsequently inflated, so as to adapt it to the identified lumen and exactly replicate the inner wall of the section of the tubular structure. Here, for example, the same method may be employed as is subsequently used in order to deform the individual elastic structure model with the elastic wall support element model.

Since the adaptation of the initial model to the lumen is intended to be carried out as rapidly and accurately as possible, the initial model is preferably assigned initial stiffness parameters which ensure that the initial model has a relatively low stiffness. After the adaptation to the section of the tubular structure, the individual structure model is then preferably assigned modified stiffness parameters to increase the stiffness of the individual structure model, so that in the end the individual structure model is finally no longer as readily deformable as the initial model. The stiffness parameters of the individual structure model are in this case particularly preferably selected so that the stiffness of the structure model is adapted to the relevant section of the tubular structure, in particular its wall material.

The initial model, and therefore also the subsequent individual structure model, are preferably constructed as a wireframe model, particularly preferably with a triangular structure. Such a wireframe model consists of node points which are connected together by a connection lines: in the case of a cylindrical model, for example, all the node points lie on a cylinder surface and neighboring points connected together by annular circumferential lines and connection lines extending diagonally and axially, so that the entire surface is composed for example of individual triangles whose vertices respectively form the node points of the model.

The adaptation of the initial model to the section of the tubular structure may be carried out with various methods, for example with a finite element method. It is, however, particularly preferable to use a method which is known as the "active contour method" or as the "snakes" method. Such a method is employed in digital image processing to determine an object contour, the object contour being described by a parametric curve whose shape, after usually manual initialization, is corrected as a function of so-called internal and external energies. The external energies are calculated from the image content in relation to the position of the contour. The internal energy is calculated only from the shape of the contour.

A minimization algorithm is used to calculate the contour shape for which the sum of all the energies reaches a minimum. A thorough description of the method may be found in the publications "Snakes—Active Contour Models" by M. Kass, A. Witkin, D. Terzopoulos in International Journal of Computervision, 1 (4): 321-331, 1987 and "Constrains on Deformable Models; Recovering 3D Shape and Nongrid Motion", also by M. Kass, A. Witkin, D. Terzopoulos, in Artificial Intelligence, 36-91-123, 1988, the entire contents of each of which are hereby incorporated herein by reference. In the scope of at least one embodiment of the present invention, the initial model is adapted by minimizing the internal and external energies to the lumen previously identified in the image data, which in fact reflects the three-dimensional contour of the inner wall of the tubular structure. This method has been found particularly suitable for application in the scope of at least one embodiment of the invention to determine the individual structure model from the initial model.

Adaptation of the individual model to the section of the tubular structure is in this case preferably carried out while taking into account a defined external force, which consists of a combination of an expansion force acting radially outward on a wall of the initial model and an oppositely directed wall resistance force that represents a resistance force of a wall of the tubular structure. For example, the two forces may be combined in a linear combination with weighting factors.

The expansion of the model is carried out stepwise, as explained in the aforementioned publication by Kass et al., by deforming the model on the basis of the external and internal forces with a particular increment in an iterative method, and then calculating the resulting energy. The method is continued until an energy minimum is finally reached.

In order to select the wall resistance force as realistically as possible, it is preferably calculated on the basis of distance image data identified from the image data of the section of the tubular structure. To this end a distance image is identified, in which image points inside the lumen of the section of the tubular structure have a predetermined constant distance value, preferably the value zero. Image points outside the lumen of the section of the tubular structure, on the other hand, have a distance value which depends on a distance, preferably the minimum Euclidian distance, of the image points from the lumen of the section of the tubular structure. This ensures that, at the positions where the model locally lies outside the lumen during the adaptation, the wall resistance force which acts on the wall of the model at the relevant point is commensurately greater as the model wall lies further outside the lumen. This means that as the distance increases, a stronger wall resistance force acts on the wall of the model at the relevant site and pulls it back inward in the direction of the lumen. In this way, particularly exact adaptation of the individual structure model to the contours of the inner wall of the tubular structure is achieved.

Currently, the adaptation of the individual model to the section of the tubular structure is carried out while taking into account a defined internal force that includes a combination of internal component forces in various directions in the wall of the initial model, the internal component forces respectively being weighted with stiffness parameters. The greater these parameters are selected to be, the greater the internal component forces and therefore the entire internal force which counteracts deformation of the model by the applied external forces. Therefore—as already described above—it is expedient for these stiffness parameters first to be selected at a relatively low level in the initial model, until optimal adaptation of the model to the lumen of the section of the tubular structure is achieved, and then, when the individual structure model has been generated, for the stiffness parameters to be stepped up in order to achieve an individual structure model which is as internally stable as possible and whose stiffness corresponds approximately to the stiffness of the real tubular structure.

So that the individual structure model remains in its shape without additional outer forces, which are for example subsequently exerted on the individual structure model by the wall support element model, after adaptation of the initial model to the section of the tubular structure the external force for the individual structure model is preferably furthermore selected according to a negative internal force of the structure model. This means that the external forces, which were previously used to adapt the initial model to the lumen while forming the individual structure model, are replaced only by an external force which, except for the direction i.e. the sign, corresponds to the internal force of the individual structure model. As explained above, except for the increased stiffness parameters, this in turn corresponds to the internal force of the original initial model. The individual structure model formed in this way is consequently stable per se without other forces.

In this individual structure model, as described, a wall support element model may then be fitted which in principle may be constructed just like the initial model or the individual structure model. This means that here again it is preferably a wireframe model, particularly preferably with a triangular structure. The dimensions, i.e. the length and the initial diameter, of the wall support element model should be selected so that they correspond to the real wall support element. Likewise, the stiffness parameters are preferably selected accordingly in order to model the wall support element as well as possible.

In order to then simulate the expansion of the wall support element inside the tubular structure, an external force must again act on this wall support element model. This is an expansion force which preferably acts radially outward. Other forces, which press outward spherically or in another way, may however also be simulated. In reality, this force may be exerted for example by placing a stent in a vessel through a balloon catheter. An external force, which counteracts this expansion force and ensures that the wall support element model is pressed back radially inward, is not achieved until a collision occurs between the wall support element model and the elastic structure model.

If a collision between the wall support element model and the individual structure model is established at a position in an expansion step, for example at a node point of the wall support element model, then a shape change of the wall support element model and the individual structure model is preferably carried out locally at least at this position while taking into account a first collision force which the structure model exerts on the wall support element model, and a second collision force which the wall support element model exerts on the structure model.

Preferably, the first collision force and/or the second collision force are proportional to a penetration depth with which the structure model and the wall support element model overlap. This means that when the structure model lies virtually outside the interior specified by the wall support element at a site in a particular step, then the force which ensures that the wall support element model is pulled back inside the structure model at this site, or that the structure model is not pressed outward at this site, is proportional to the overlap distance. To first approximation, the force definition corresponds very well to reality and ensures that the wall support element model is guaranteed to finally lie inside the structure model in the simulation. The first and second collision forces may have the same magnitude but be directed oppositely to one another.

In the individual expansion steps, the extent to which the structure model is locally pressed outward at this site depends not only on the collision forces but also on the stiffnesses of the structure model and the wall support element model, on the one hand, and the expansion force still acting on the wall support element model on the other hand.

The expansion force may in this case be selected so that it decreases with an increasing radius of the wall support element model, i.e. it becomes commensurately less when the wall support element model has already expanded more. It is however also possible to assume a constant expansion force throughout the simulation up to a predetermined maximum size which in reality, for example when fitting a stent, may correspond to the maximum diameter of the stent. After this diameter is reached, the invention expansion force may be reduced.

In order to accelerate the simulation, it is possible to ensure that an increment in an expansion step is selected at least locally as a function of at least one collision force identified in a preceding expansion step between the structure model and the wall support element model. In this case, for example, it is possible to ensure that the first expansion steps are relatively large in order to achieve rapid expansion. Smaller increments are not selected until a collision occurs between the wall support element and the structure model, so as to achieve a maximally accurate simulation.

The simulation method according to at least one embodiment of the invention is preferably employed within a method for driving an image display device for displaying image data of the interior of a tubular structure. The structurally individualized simulation of how a wall support element is introduced into a section of a tubular structure is carried out with the simulation method. This simulation result, i.e. in particular the expanded wall support element, may then be represented on the image display device together with the image data of the interior of the tubular structure.

For example, the expanded wall support element and optionally the individual structure model may simply be superimposed with the image data on the image display device in the appropriate position, so that it is possible to represent how the wall support element becomes positioned inside the tubular structure after introduction. In an example variant, it is in this case also possible for the data from the simulation, which describe the shape of the structure model, to be used in order to manipulate the image data so that a predicted shape of the tubular structure after fitting the wall support element is represented to the user. For example, in the case of fitting a stent in a vessel, the vessel representation inside the tomography section images may be manipulated so that the inner contours of the vessel correspond to the contours of the structure model after fitting the wall support element model. In this way, an operator can receive a very realistic preview of the result of the subsequent intervention, which facilitates selection of an appropriate stent.

BRIEF DESCRIPTION OF THE DRAWINGS

The invention will be explained in more detail below with the aid of an example embodiment with reference to the appended drawings, in which.

DETAILED DESCRIPTION OF THE EXAMPLE EMBODIMENTS

Figure 1:
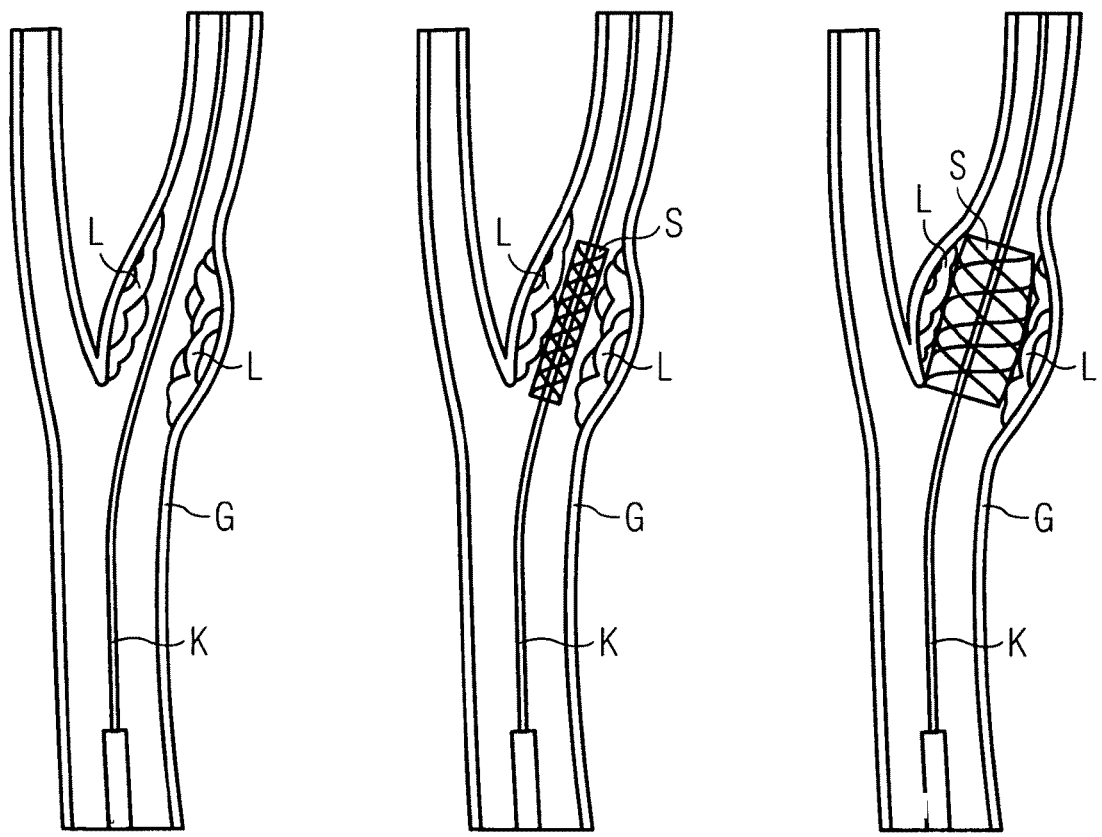
FIG. 1 shows an outline representation of the introduction of a stent for treating a carotid stenosis.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another.

For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The following example embodiment involves the simulation of the introduction of a stent S into a carotid artery G. For simplicity, therefore, the term "stent model" will also be used instead of the term "wall support element model", and the term "vessel model" or "carotid model" will be used instead of "structure model". Embodiments of the invention are however expressly not restricted to this application, but may also be used for the introduction of a stent into other vessels or other tubular structures in the body, for example an esophagus, trachea or the like. Likewise, as already explained in the introduction, embodiments of the invention may possibly be employed in the non-medical field when stent-like inserts need to be fitted into tubes or hoses in engineering systems or the like.

FIG. 1 shows an outline of the introduction of a stent S into a vessel G, and has already been explained in the introduction.

Figure 9:
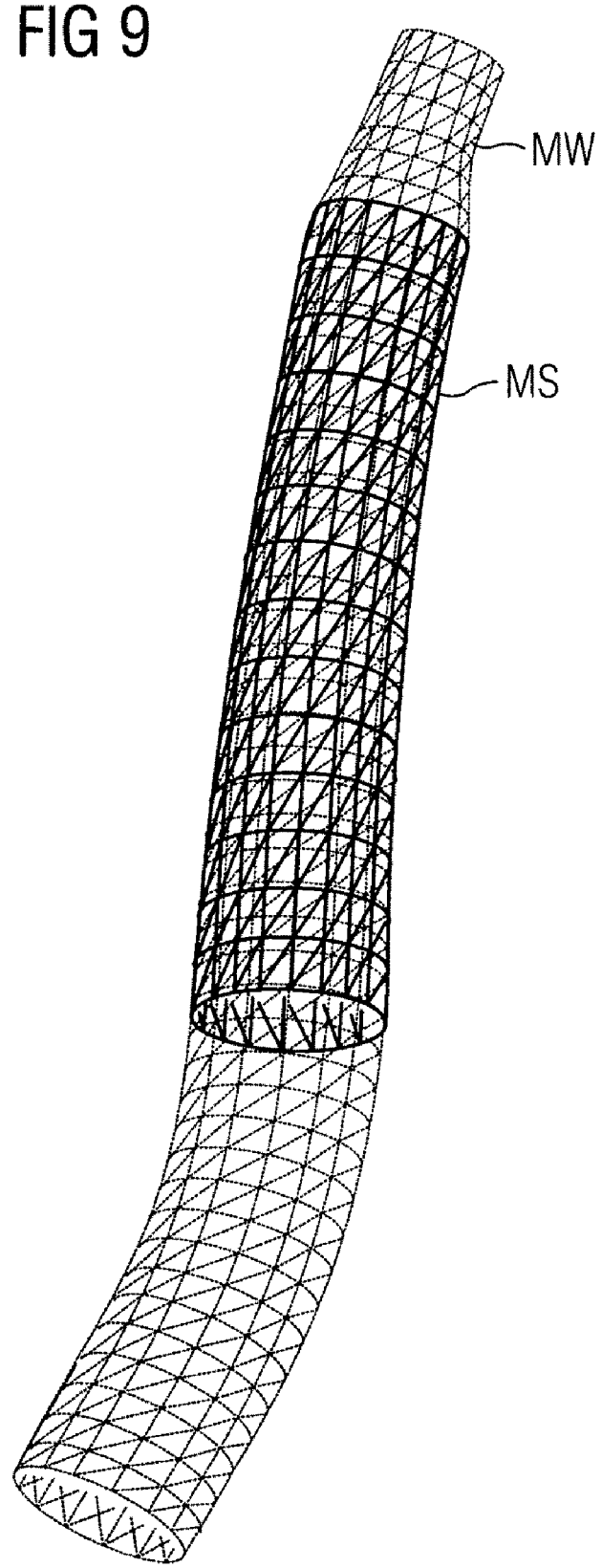
FIG. 9 shows a representation of the structure model containing with a stent model, as in FIG. 7, but now with an expanded stent model.
Figure 10:
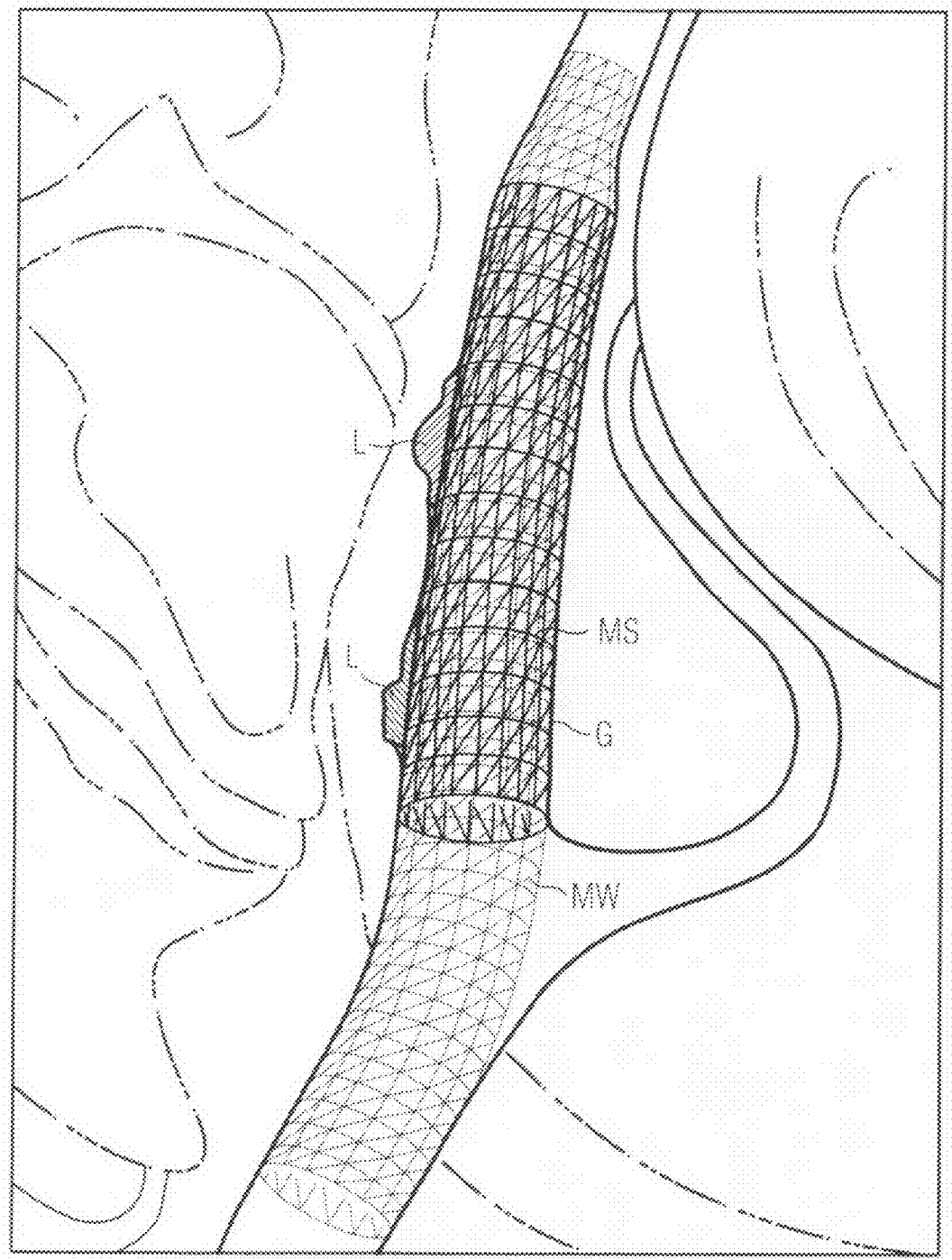
FIG. 10 shows an overlay of the model according to FIG. 9 with the computer tomography section image according to FIG. 2.
Figure 11:
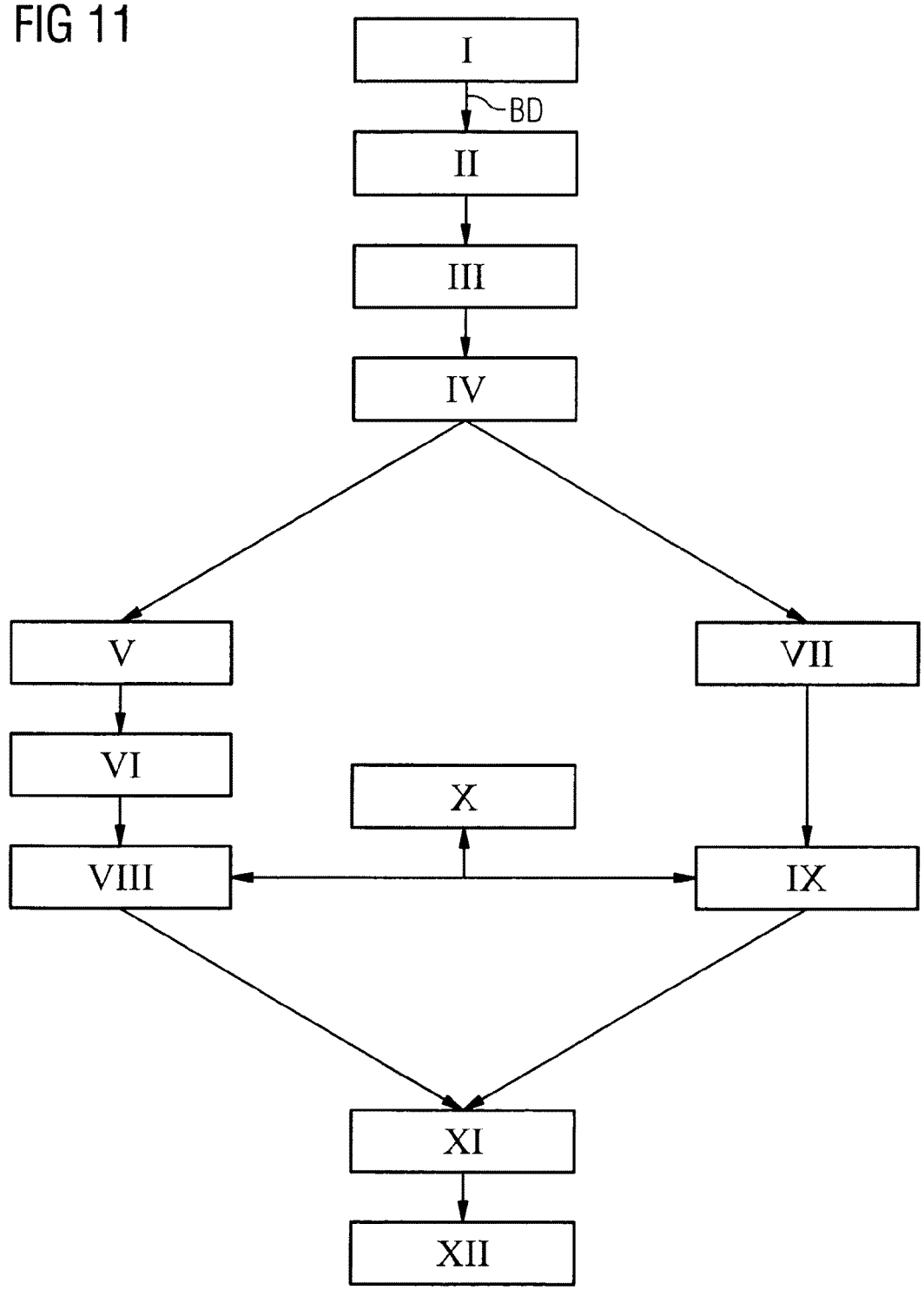
FIG. 11 shows a flowchart to represent a possible sequence of a simulation method according to an embodiment of the invention.

FIGS. 2 to 10 contain various graphical representations to explain individual method steps of the method, and FIG. 11 shows an overview of a possible overall sequence of the method in the form of a flowchart.

Figure 2:
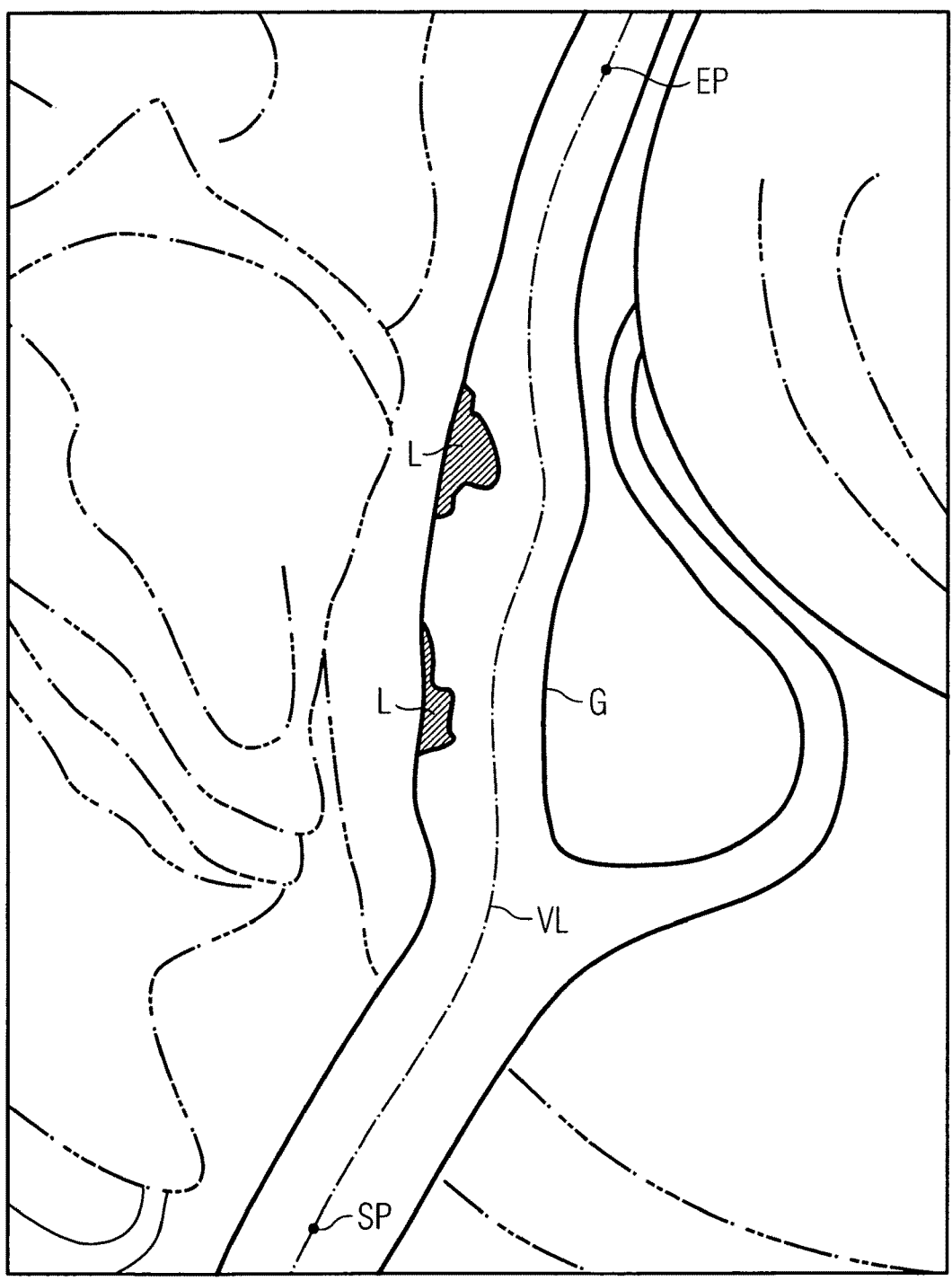
FIG. 2 shows a schematic representation of a computer tomography section image through a carotid artery with two stenosis sites and a central line through the carotid artery along the branch with the stenosis sites.

In a first method step I according to FIG. 11, image data are read in, for example magnetic resonance tomography data or computer tomography data, which have previously been made by a corresponding system of the patient's relevant vascular region for which the current simulation is intended to be carried out. FIG. 2 schematically represents a two-dimensional computer tomography section image of the vessel G, i.e. here a carotid artery G, with two stenosis sites L.

Before a simulation of the stenosis placement can be carried out, the three-dimensional image data BD, on the basis of which for example the section image according to FIG. 2 was generated, are preprocessed by segmenting the vessel in the image data BD. To this end a start point SP and an end point EP, which define the section of the carotid artery G to be addressed within the simulation method, are initially marked in step II. The start point SP and the end point EP may, for example, be set by the operator by means of a suitable graphical user interface.

In step III, the segmentation of the lumen of the vessel can be carried out. To this end a seed point-based region growth method may be used, which classifies the voxels inside the vessel by their intensity values. The start point SP and/or the end point EP may be employed as seed points for the region growth method. Such seed point-based region growth methods are known to the person skilled in the art and need not therefore be explained in detail here. The contours of the inner wall of the vessel to be addressed can also be identified by the segmentation of the lumen of the vessel.

Subsequently, in a step IV, a centerline through the vessel section is determined and a so-called distance image is furthermore calculated from the image data. The determination of the centerline VL may be carried out with various known methods, for example the Dijkstra algorithm. A skeletization algorithm is preferably used, as is described in the publication "New Vessel Analysis Tool for Morphometric Quantification and Visualization of Vessels in CT and MR Imaging Data Sets" by T. Boskamp, D. Rinck, F. Link, B. Kuemmerlen, G. Stamm and P. Mildenberger in Radiographics 24, 2004, the entire contents of which are hereby incorporated herein by reference.

In order to compile the distance image, all the voxels inside the lumen of the vessel G simply assigned the distance value zero. Voxels outside the lumen receive a value which represents the minimum Euclidean distance to the inner wall contour, i.e. to the contour of the lumen.

The individual vessel model is subsequently identified in steps V and VI, and an initial stent model is provided or generated in step VII. As represented in FIG. 11, these steps may take place in parallel. In principle, however, it is also possible to carry out these steps in succession, for example initially identifying the individual vessel model in steps V and VI and then the initial stent model.

Figure 3:
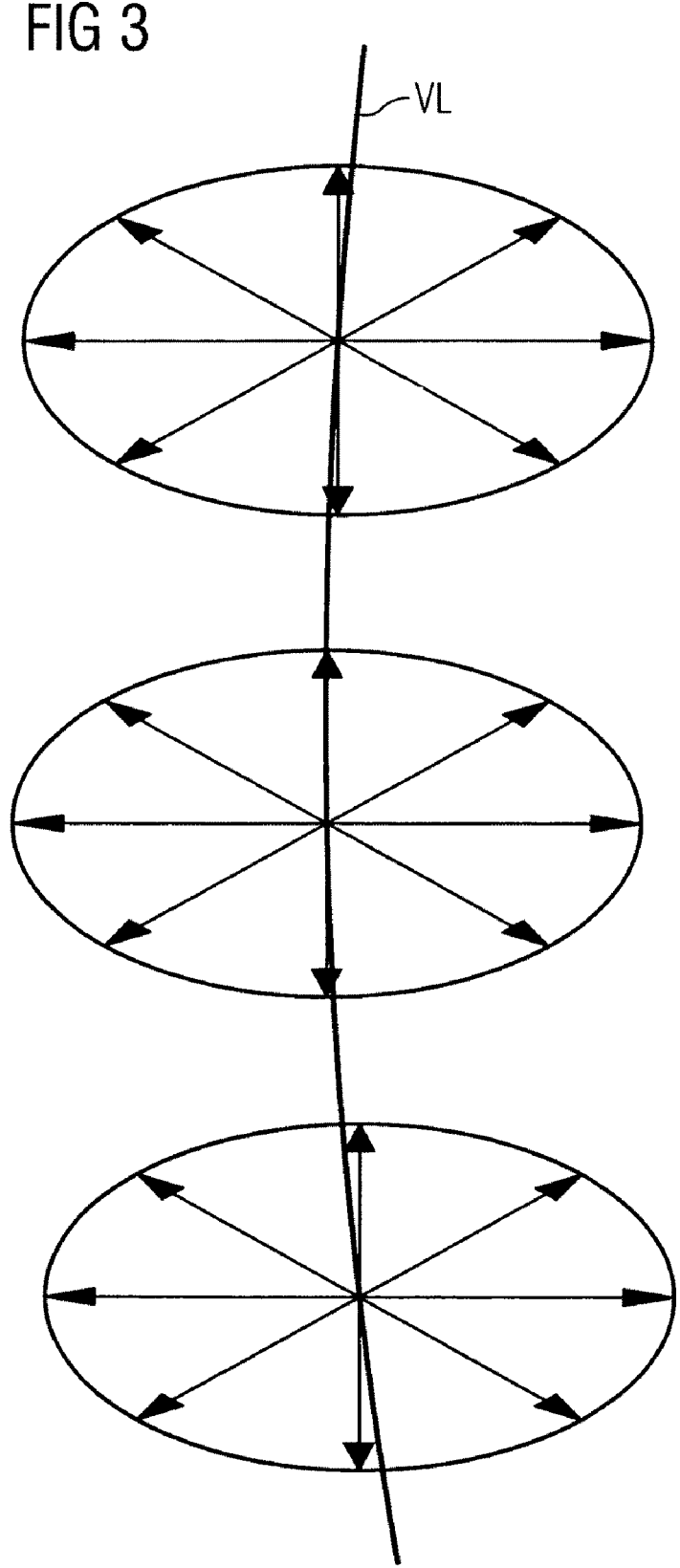
FIG. 3 shows a schematic representation of such a central line and radial rays extending therefrom to explain the structure of and elastic structure model.

The identification of the vessel model MW is initially carried out with an identification of an initial model MWI in step V. In order to construct this initial model, rays extending radially outward with a particular length from the centerline VL are respectively identified at points lying on the centerline VL at particular, preferably equidistant spacings between the start point SP and the end point EP. This is represented in FIG. 3. The length of the rays is selected so that it lies below the minimum radius of the vessel lumen in the section to be modeled. The end points resulting from this, which respectively lie on a circular line around the point on the centerline VL from which the rays radiate, are then the node points of the initial model MWI. They are respectively connected together to form triangular surfaces, as is shown in the representation on the left-hand side of FIG. 7. This creates a grid network with a cylindrical surface composed of triangular faces, this initial model being adapted in its length profile to the centerline VL of the vessel G, since the centroids of the node points respectively lying on a circular ring lie exactly on the centerline VL.

Figure 4:
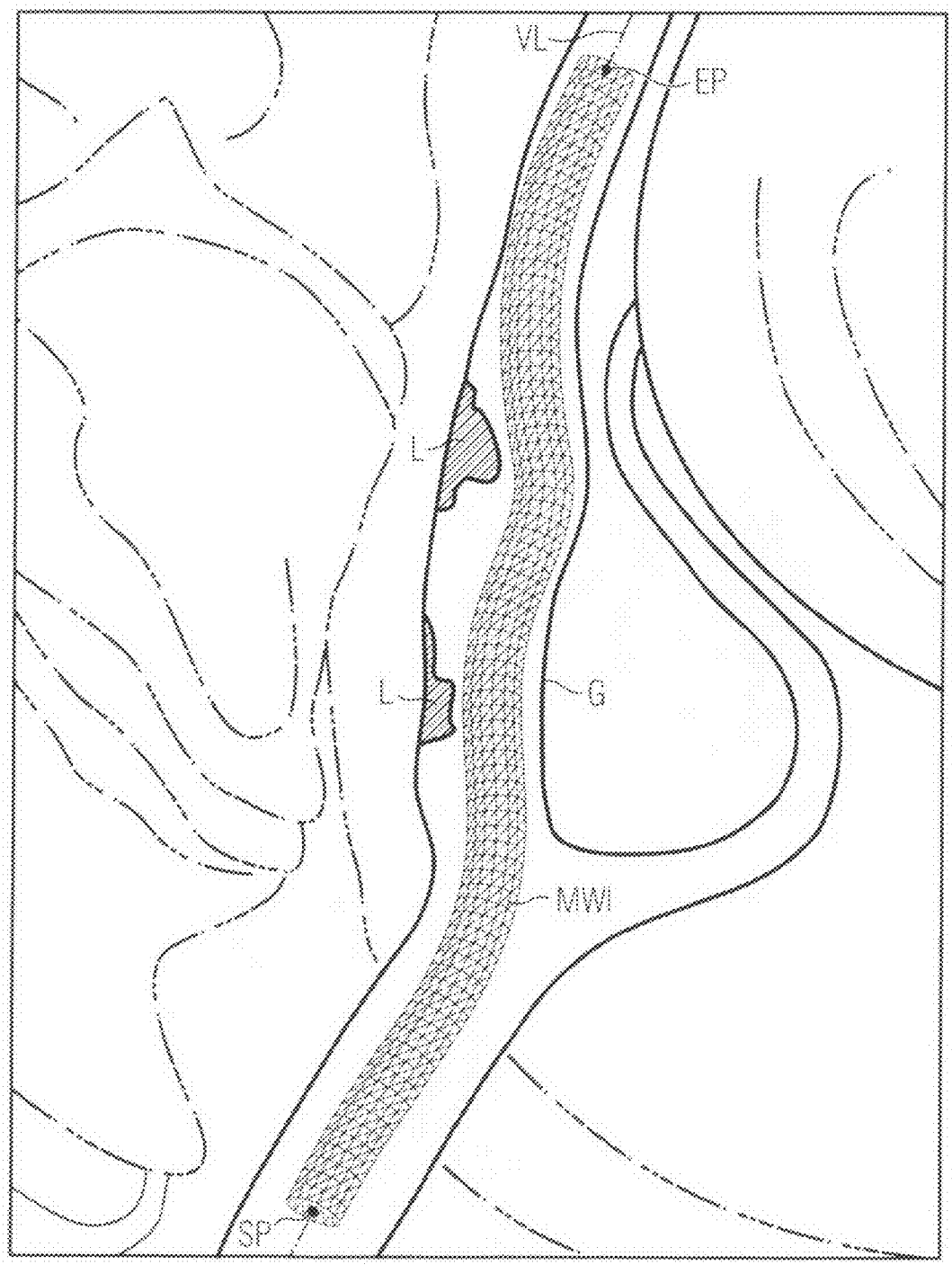
FIG. 4 shows a representation of the computer tomography section image of the carotid artery, as in FIG. 2, but now with an initial model extending along the central line.

FIG. 4 shows the situation in which the initial model MWI extends between the start point SP and the end point EP along the centerline VL through the carotid artery G.

In a next step VI, this initial model MW is then adapted to the contours of the lumen of the vessel G in a three-dimensional active contour method, similarly as is described in detail in the documents by Kass et al. already cited above, the entire contents of which are hereby incorporated herein by reference.

In the scope of the active contour method, external and internal forces which deform the initial model MWI are simulated. The deformation of the model wall takes place so that the energy function $$E = \int_{t=0}^{1} \int_{s=0}^{1} E_{int}(v(s,t)) + E_{ext}(v(s,t)) \, ds \, dt \tag{1}$$

is minimized. In this case, the variable v(s,t) represents the surface points of the model, s and t being cylindrical coordinates which are defined here so that they range from 0 to 1, although they may also be normalized in any other desired way. For example, s may be the axial coordinate which specifies the position of a ring along the centerline VL, and t the angle coordinate i.e. the orientation of the surface point on the respective ring.

$E_{int}$ are the internal energy is in the model and $E_{ext}$ the external energies. E is the resulting total energy. The external energy $E_{ext}$ is given by the external force $F_{ext}$, which is in turn composed of two individual external forces $F_{vw}$ and $F_{exp}$ according to $$F_{ext} = w_{vw} F_{vw} + w_{exp} F_{exp}. \tag{2}$$

Here, $w_{vw}$ and $w_{exp}$ are two weighting functions which determine the ratio mutual of the forces and the level of the total external force $F_{ext}$. They may, for example, be selected between 0.5 and 1.0. The force $F_{exp}$ is an expansion force, which has a dilating effect on the initial model MWI and presses the individual node points of the initial model MWI radially outward against the wall of the carotid artery G. The direction thus corresponds to the arrow directions in FIG. 3. In order to calculate this expansion force $F_{exp}$, the centroid is calculated for each ring of the initial model MWI unless it is already known from the compilation of the initial model, or has been stored, or if for example forces are actually intended to be calculated at all points on the triangular surfaces for the expansion. The vectors from the central point of each ring to the points on the ring can then be calculated, similarly to the radial rays which are represented in FIG. 3. The vectors then represent the direction of the expansion forces $F_{exp}$, which act on the ring at each individual point.

The force $F_{vw}$ is a vessel wall force, which acts inward when the vessel model emerges from the lumen at a site during the active contour method, i.e. when the model lies outside the vessel wall during the adaptation of the model. The absolute value of this force $F_{vw}$ is given by the equation $$F_{vw} = D(x, y, z) \nabla D(x, y, z). \tag{3}$$

D(x,y,z) is the aforementioned distance image of the segmented vessel G, (x,y,z) indicating the coordinates of a particular voxel position. In this way, the resistance of the vessel wall is simulated. The vessel wall force $F_{vw}$ is therefore proportional to this distance image value D(x,y,z) and to the gradient $\nabla D(x,y,z)$.

The elastic behavior of the initial model MWI, or of the individualized vessel model MW developed using it, is simulated by internal forces $E_{int}$ in a horizontal, vertical and diagonal direction. For the horizontal and vertical forces, the first and second partial derivatives of the coordinates s and t are calculated. The mixed derivatives for the diagonal forces are additionally required in order to obtain the function of the internal energy $E_{int}$.

$$E_{int} = w_1 \frac{\partial v(s,t)}{\partial s} + w_2 \frac{\partial v(s,t)}{\partial t} + w_3 \frac{\partial^2 v(s,t)}{\partial s^2} + w_4 \frac{\partial^2 v(s,t)}{\partial t^2} + w_5 \frac{\partial^2 v(s,t)}{\partial s \partial t} \tag{4}$$

Each derivative has a weighting factor $w_i$, i=1 to 5. These define the stiffness behavior of the model wall. The greater the weighting factors $w_i$ are, the stiffer the model is. The weighting factor $w_1$ determines the stiffness in the longitudinal direction of the model, and the weighting factor $w_2$ determines the stiffness in the circular direction i.e. along the individual rings. The other weighting factors $w_3$, $w_4$, $w_5$ respectively determine the diagonal stiffnesses. The weighting factors $w_i$, i.e. the stiffness parameters for the individual coordinates of the initial model MWI, or of the vessel model MW, may respectively be combined in a stiffness matrix and stored, so that they can then be accessed later in the method. So that the initial model MWI can be adapted sufficiently accurately to the contours of the vessel G in a short computing time $w_i$, small values are preferably selected for the weighting factors, for example values of 0.1 or less.

The internal forces $F_{int}$ are given as the derivative of this internal energy $E_{int}$, i.e. $F_{int} = \nabla E_{int}$. Likewise, $F_{ext} = \nabla E_{ext}$. In order to achieve the objective that the energy function defined in Equation (1) and the minimized, the following Euler-Lagrange equation may accordingly be solved:

$$-\nabla E_{ext} = -\frac{\partial}{\partial s}\left(w_1 \frac{\partial v}{\partial s}\right) - \frac{\partial}{\partial t}\left(w_2 \frac{\partial v}{\partial t}\right) + \frac{\partial^2}{\partial s^2}\left(w_3 \frac{\partial^2 v}{\partial s^2}\right) + \frac{\partial^2}{\partial t^2}\left(w_4 \frac{\partial^2 v}{\partial t^2}\right) + 2\frac{\partial^2}{\partial s \partial t}\left(w_5 \frac{\partial^2 v}{\partial s \partial t}\right) \quad (5)$$

Solution methods required for this are known to the person skilled in the art; for example, solution methods may be found in the cited documents by Kass et al. In particular, numerical solution of the equation is also possible within the simulation method.

Figure 5:
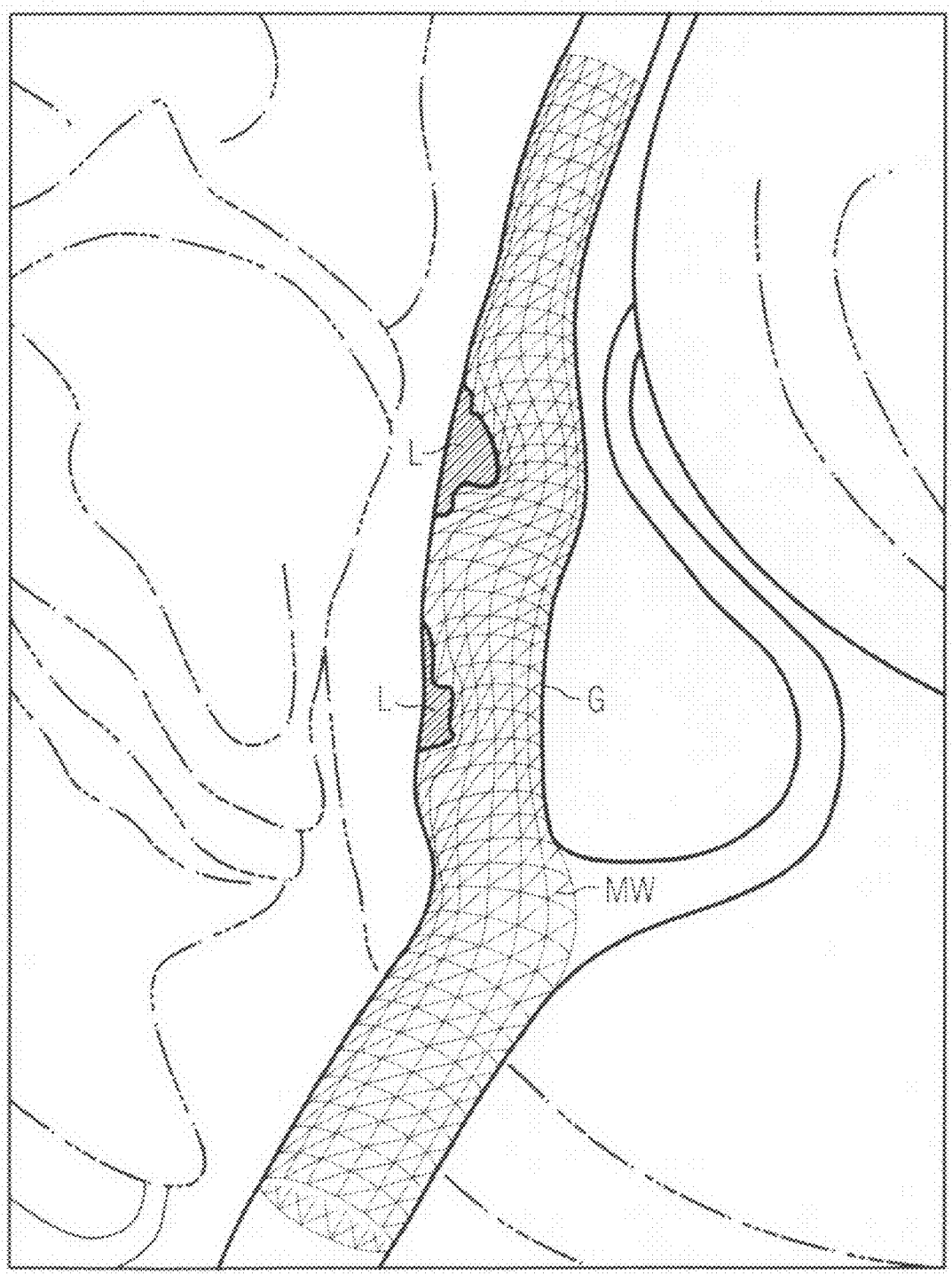
FIG. 5 shows a representation of the carotid artery, as in FIG. 4, this time with an individual structure model adapted to the lumen of the carotid artery.

FIG. 5 shows the individualized vessel model MW, adapted to the inner contour of the vessel G, which is superimposed with the image data BD of the vessel G.

After the initial model MWI has thus been adapted to the contours of the lumen of the vessel G final compilation of the individualized vessel model MW requires modification of the internal and external forces. On the one hand, the stiffness matrix is modified so that the physical stiffness behavior is modeled as realistically as possible by the large internal forces actually existing in the vessel wall, i.e. the individual stiffness parameters or weighting factors $w_i$ are stepped up, for example to a value of between 0.5 and 1. Furthermore, the individualized vessel model MW should also be stable per se even without external forces. This means that the vessel model MW should be kept in an equilibrium state with the stiffness matrix then obtained, but without deriving the reaction force of the wall from the rigid segmentation of the data set. To this end, instead of the previous external forces $F_{ext}$ as were specified according to Equation (2) for the initial model MWI, only one external force $F_{extW}$ is now defined which is set equal to the internal forces $F_{int}$ in this deformation state.

$$F_{extW} = -\nabla E_{int} = -F_{int} \quad (6)$$

Owing to this quasi-plastic deformation, the vessel model MW remains unchanged in the following iteration steps unless a further external force acts on the vessel model MW. In order to obtain the negative internal forces for determining the external forces $F_{extW}$ according to Equation (6), an iteration step is carried out without external energies, and the differences between the grid coordinates before and after the iteration step are compared.

The generation of the stent model MS in step VII is carried out similarly to the generation of the initial model MWI. The stent model then in principle has the same surface topology as the initial model MWI, i.e. it is also an essentially cylindrical model in which the nodes are arranged on rings on different centerline planes. The only difference is that the length of the stent model MS is less than the length of the vessel model MW. This is preferably selected so that it corresponds to the length of a real stent selected for the case in question. Likewise, the initial radius of the rays radiating from the centerline VL (cf. FIG. 3) will be selected according to the radius of the desired stent before expansion of the stent. This stent radius must thus be selected so that it is less than the minimum radius of the lumen, and naturally also less than the minimum radius of the vessel, from the site at which the catheter is inserted into the vessel to the site where the stent is intended to be positioned, so as to be able to take the stent through the catheter to the appropriate position.

Figure 6:
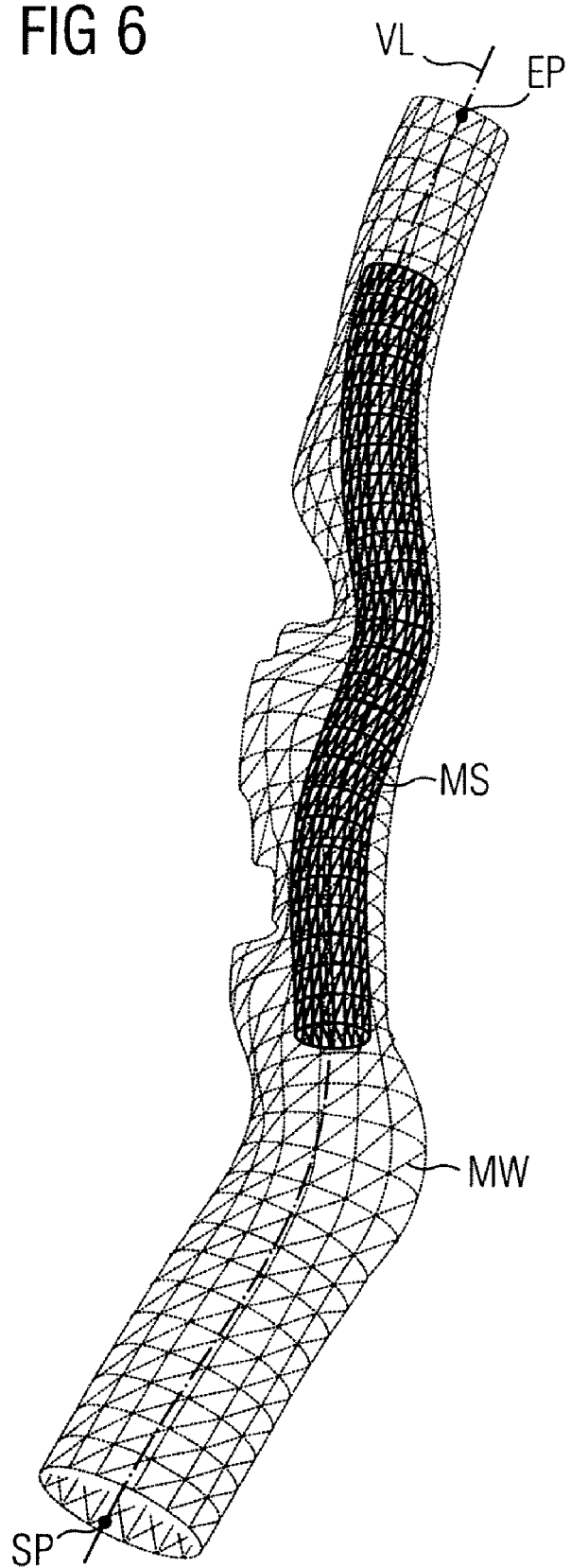
FIG. 6 shows a representation of the structure model according to FIG. 5 with a stent model arranged in it before expansion.

FIG. 6 shows the individualized vessel model MW generated according to the preceding method steps with the unexpanded stent model MS, after it has been positioned there with the (virtual) catheter, for example by the operator having specified by way of a user interface the distance at which, i.e. where on the centerline VL, the stent model MS with the defined length is intended to lie before expansion inside the vessel model MW. This may be done by defining a start point or an end point for the stent model, similarly as the start point SP and the end point EP were established for the vessel model MW. If the length of the stent or the stent model MS is specified, then defining a point is sufficient for the positioning.

In step IX, the stent model MS is then expanded. This again requires an expansion force $F_{expS}$, which for example in reality is generated by a balloon catheter and presses the stent outward. This means that an external force $F_{extS}$ according to the equation $$F_{extS} = w_{expS} F_{expS} \quad (7)$$

acts on the stent at the start of the expansion (similarly to Equation (2)).

Furthermore, here again the elastic behavior of the stent model MS may be taken into account through internal forces in a horizontal, vertical and diagonal direction similarly to Equation (4).

The crucial point is that collisions between the vessel model MW and the stent model MS occur during the expansion of the stent model MS. This leads to deformation of the vessel model MW, which is represented by method step VII in FIG. 11. To this end, in method step X, the collisions between the stent model MS and the vessel model MW are continuously determined during the expansion of the stent model MS. The collision detection is based on a method such as is described in more detail for example in DE 10 2007 039 207 A1, the entire contents of which are hereby incorporated herein by reference. In order to check whether a collision has taken place at a particular point, rays are constructed in each iteration step, starting from points which lie inside the stent model MS and extending two points of the stent model MS which are intended to be checked for collision. This procedure is schematically represented in FIGS. 7 and 8.

Figure 7:
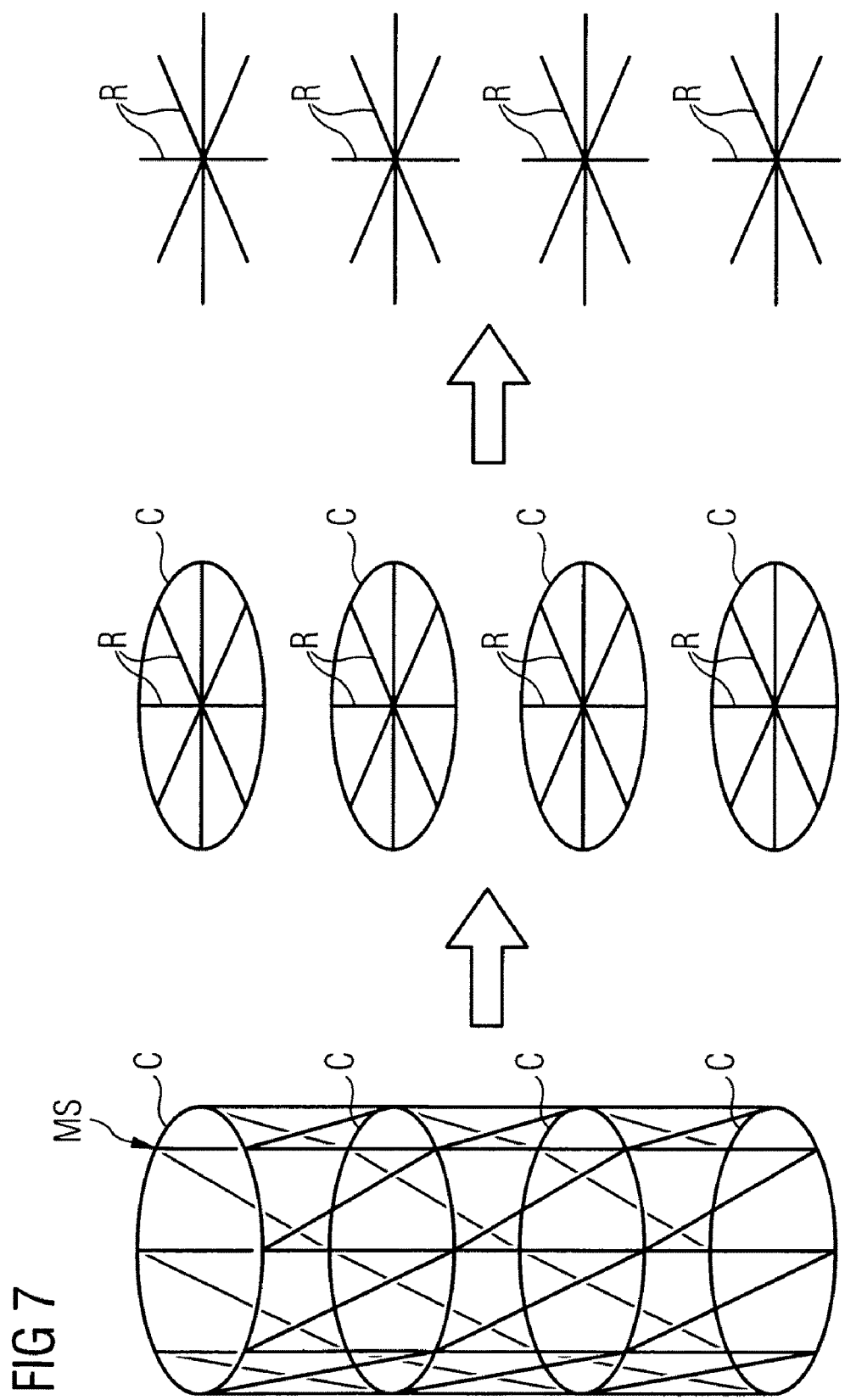
FIG. 7 shows a schematic representation to explain the structure of a triangular wireframe model as a stent model and to explain the check for collisions with a structure model.

The left-hand side of FIG. 7 shows the stent model MS composed of triangular faces, and the central illustration shows the way in which the rays R are constructed starting from points inside the model, these points respectively being the centroids for each ring C and the rays R extending from these points respectively to the corresponding ring points on the surface of the stent model MS (see central picture). The right-hand representation then merely shows the constructed radial rays R which are used in order to check for a collision with the vessel model.

Figure 8:
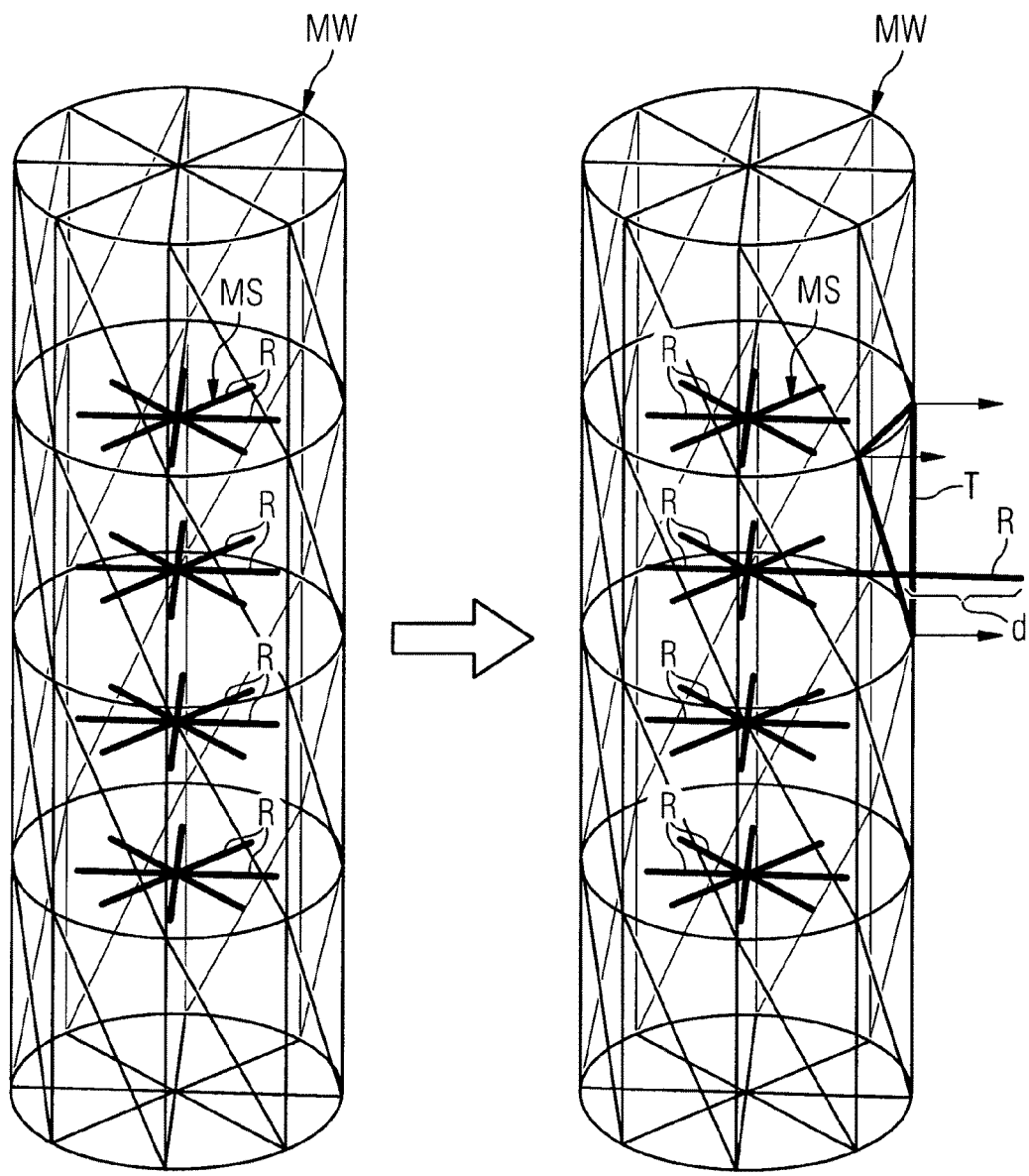
FIG. 8 shows two further representations to explain the collision check between the stent model and the structure model.

This check is schematically visualized in FIG. 8. There, the left-hand side represents a section of the vessel model MW, in the interior of which the above-explained radially extending rays R of the stent model are shown, which here symbolize the stent model MS. The right-hand side represents by way of example a situation in which a collision has occurred between the stent model and the vessel model MW, which is demonstrated by the fact that one of the radial rays R of the stent model passes through a triangular face T of the vessel model MW. A suitable method for determining intersections of rays having a defined length with triangular faces is described, for example, in the publication "Fast, Minimum Storage Ray-Triangle Intersection" by T. Möller and B. Trumbore in Journal of Graphic Tools, 2 (1): 21-28, 1997, the entire contents of which are hereby incorporated herein by reference. It is thus merely necessary to check whether such an intersection occurs.

When a collision occurs between the stent model and the vessel model, the stent model presses against the vessel model MW from the inside and expands it. The forces acting on the triangular face of the vessel model MW are symbolized in FIG. 8 by arrows at the node points. The extent to which the stent model MS can expand, and how the vessel model can be deformed MW, depend here essentially on the stiffness parameters of the stent model MS and of the vessel model MW.

In order to describe the interaction between the vessel model and the stent model more accurately in the simulation, the external forces $F_{extS}$ and $F_{extW}$ of the stent model and of the wall model are augmented by corresponding collision forces $F_{ColW}$, $F_{ColS}$:

$$F_{extS} = w_{expS} F_{expS} + F_{ColW} \quad (8a)$$

$$F_{extW} = -\nabla F_{int} + F_{ColS} \quad (8b)$$

So long as no collision occurs, the collision forces $F_{ColS}$, $F_{ColW}$ are equal to zero and the vessel model MW does not change during the iteration steps in the expansion of the stent model MS. As soon as a collision occurs, the collision forces may for example be selected according to the following equation locally at the respective point where the collision has taken place:

$$F_{ColW} = c_{ColW} \cdot d \quad (9a)$$

$$F_{ColS} = -c_{ColS} \cdot d \quad (9b)$$

This means that the collision forces $F_{ColW}$, $F_{ColS}$ are oppositely directed and defined proportionally to a penetration depth d, which indicates how far the respective radial ray R of the stent model has penetrated through the triangular face T of the vessel model, as represented in FIG. 8. The factors $c_{ColW}$ and $c_{ColS}$ may in particular also be selected to be equally large, so as to represent that the collision forces on the two models are each of equal size and merely oppositely directed in vector terms.

When the balloon force $F_{expS}$ which presses the stent model MS outward is selected to be large enough, the effect of this is that the stent model MS is capable of expanding up to its maximum diameter which may be specified, for example, by the internal forces of the stent model MS but also by the definition of the balloon force $F_{extS}$. Expansion to the maximum diameter then ensures that the vessel model MW is widened accordingly, as represented in FIG. 9.

Such an image may, for example, be displayed in step XI as the result of the simulation. Furthermore, as an alternative or in addition, it is possible to present a display of the simulation result according to FIG. 9 simultaneously with a superimposed CT image of the vessel G, as is schematically represented in FIG. 10. It is in this case also possible to use the simulation results in order to virtually visualize the walls of the vessel and its expansions by corresponding manipulations of the CT image, i.e. the stenoses L are pressed outward here and the vessel G, in the region of the stent S, again has a diameter which ensures sufficient flow.

The simulation results may furthermore, for example, be used in a step XII in order to select a suitable stent, i.e. a stent with a suitable length, suitable initial and maximum diameter and suitable stiffness. All these values have in fact been taken into account in the simulation, and accordingly may also be interrogated by the operator. Conversely, it is also possible for the operator to select a defined initial stent model MS matching a particular a real stent, so that all the internal forces, the initial radius, the length and the maximum deployment radius for the stent model MS are then specified automatically. If the simulation does not lead to a satisfactory result, the operator may select a new stent model MS for another stent, in order to check whether improved results are thereby obtained. This means that the steps VII to XII may be carried out several times in the scope of the method according to the invention with different stent models MS, so as to obtain an optimal result in step XII for the stent selection.

Figure 12:
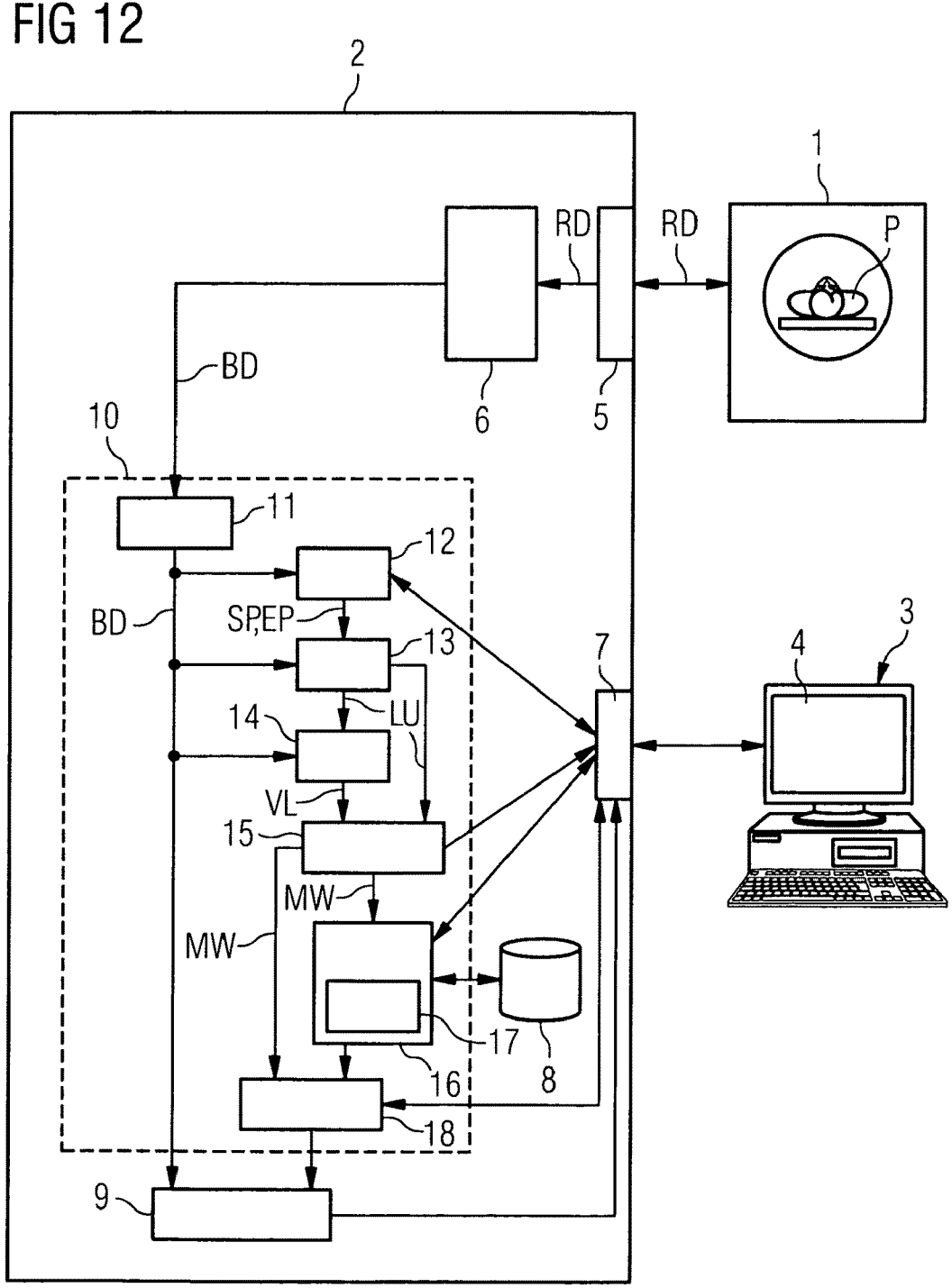
FIG. 12 shows a schematic block diagram of a simulation device according to an embodiment of the invention.

FIG. 12 shows a schematic image of a simulation device 10 according to an embodiment of the invention, which is embodied here primarily in the form of software modules on a computer unit 2, for example by the software modules being implemented on a processor or a plurality of interacting processes. The computer unit 2 has a terminal interface 7, via which a terminal 3 is connected to a display device 4, for example a conventional monitor. A raw data interface 5 allows connection to a computer tomography instrument 1, in which a patient P can be positioned. Then, for example, raw data RD are acquired in the computer tomography unit instrument 1, transferred to the interface 5 and from there on to an image reconstruction device 6 so as to reconstruct computer tomography image data BD of a vessel of the patient P, in whom a stent is to be fitted.

The image data BD generated in this way are transferred to an image data interface 11 of the simulation device 10.

A position determination unit 12 is used to determine the start point SP and the end point EP of the section of the vessel. This position determination unit 12 interacts with the terminal 3 in that the image of the vessel is represented on the display device 4 with a graphical user interface, and the user can set the points SP, EP with a suitable peripheral device, for example a mouse (not shown).

The illuminant determination unit 13 is used to segment the lumen of the vessel G in the manner described above with a region growth method. A distance image may furthermore be generated in this lumen determination unit 13.

In a profile online determination unit 14, the centerline VL of the section of the vessel G is then identified in the manner described above.

The centerline VL and the lumen LU are furthermore used in a structure model identification unit 15 in order to generate an individual elastic structure model MW or vessel model MW from and elastic initial model MWI in the manner described above. The individual vessel model MW generated in this way may then, for example, be presented to the operator on the display device 4 (see FIG. 6).

A wall support element model identification unit 16 with a positioning unit 17 is used to select a stent model MS and position it appropriately, as was described above. To this end finished stent models, or at least certain parameters for various real stents, may be stored in a memory 8.

An expansion unit 18 is lastly used to virtually expand the stent model MS stepwise in the manner described above, while respectively taking into account collisions between the stent model MS and the individual vessel model MW and deforming the vessel model MW accordingly.

The result is processed with a visualization device 9, which may also superimpose the result of the image data BD as described above, and finally delivered to the operator on the display 4 (see FIG. 10).

As the present example embodiment shows, the invention thus offers a very rapid and practical method, and a corresponding simulation device, for a simulating the placement of the stent in a vessel. The elastic method takes into account the real wall vessel. Only very few interactions by the operator are required for the simulation, for example selecting a stent model and determining the start and end points of the section of the vessel which is intended to be addressed in the simulation. In particular, it is possible to compile the individualized vessel model fully automatically and extraordinarily rapidly.

To conclude, it is once more to be pointed out that the method described in detail above and the simulation device merely constitute preferred example embodiments, which may be modified in a wide variety of ways by the person skilled in the art without departing from the scope of the invention, as it is specified by the claims. For the sake of completeness, it is also to be pointed out that the use of the indefinite article "a" or "an" does not exclude the possibility that there may also be several of the relevant features present. Likewise, the terms "unit" or "module" etc. do not exclude the possibility that they may consist of a plurality of components which, optionally, may even be spatially distributed.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for structurally individualized simulation of the introduction of a wall support element into a section of a tubular structure, the method comprising:
   providing image data, which includes at least image data of the interior of the section of the tubular structure;
   determining a start point and an end point of the section of the tubular structure;
   determining a lumen of the section of the tubular structure between the start point and the end point on the basis of the image data;
   determining a profile line between the start point and the end point on the basis of the image data;
   identifying an individual elastic structure model for the section of the tubular structure by adapting a tubular elastic initial model to the section of the tubular structure on the basis of the identified lumen and the profile line;

providing a tubular elastic wall support element model which is positioned inside the individual structure model; and stepwise virtual expanding of the wall support element model, a check for collisions between the wall support element model and the individual structure model being carried out in each virtual expanding step, and the wall support element model and the individual structure model being modified at least locally at the positions where a collision is identified, while taking into account the elasticity of the individual structure model.

2. The method as claimed in claim 1, wherein initial stiffness parameters are assigned to the initial model, and wherein modified stiffness parameters are assigned to the individual structure model after the adaptation to the section of the tubular structure, in order to increase the stiffness of the individual structure model.

3. The method as claimed in claim 2, wherein the stiffness parameters of the individual structure model are selected so that the stiffness of the individual structure model is adapted to the relevant section of the tubular structure.

4. The method as claimed in claim 2, wherein at least one of the initial model and the wall support element model are constructed as a wireframe model.

5. The method as claimed in claim 1, wherein the stiffness parameters of the individual structure model are selected so that the stiffness of the individual structure model is adapted to the relevant section of the tubular structure.

6. The method as claimed in claim 1, wherein at least one of the initial model and the wall support element model are constructed as a wireframe model.

7. The method as claimed in claim 1, wherein the adaptation of the individual model to the section of the tubular structure is carried out with an active contour method.

8. The method as claimed in claim 1, wherein an adaptation of the individual model to the section of the tubular structure is carried out while taking into account a defined external force, which includes a combination of an expansion force acting outward on a wall of the initial model and a wall resistance force that represents a resistance force of a wall of the tubular structure.

9. The method as claimed in claim 8, wherein the wall resistance force is calculated on the basis of a distance image data identified from the image data of the section of the tubular structure, image points inside the lumen of the section of the tubular structure having a constant distance value and image points outside the lumen of the section of the tubular structure having a distance value which depends on a distance of the image point from the lumen of the section of the tubular structure.

10. The method as claimed in claim 8, wherein after the adaptation of the initial model to the section of the tubular structure, the external force for the individual structure model is selected according to a negative internal force of the individual structure model.

11. The method as claimed in claim 1, wherein an adaptation of the individual model to the section of the tubular structure is carried out while taking into account a defined internal force that includes a combination of internal component forces in various directions in the wall of the initial model, which are respectively weighted with stiffness parameters.

12. The method as claimed in claim 1, wherein, when a collision between the wall support element model and the individual structure model takes place at a position in an expansion step, a shape change of the wall support element model and the individual structure model is carried out at least at this position while taking into account a first collision force which the structure model exerts on the wall support element model, and a second collision force which the wall support element model exerts on the structure model.

13. The method as claimed in claim 12, wherein at least one of the first collision force and the second collision force are proportional to a penetration depth with which the structure model and the wall support element model overlap.

14. The method as claimed in claim 12, wherein an increment in an expansion step is selected at least locally as a function of at least one collision force identified in a preceding expansion step between the structure model and the wall support element model.

15. The method as claimed in claim 1, wherein the wall support element is a stent and the tubular structure is a vessel.

16. A method for driving an image display device for displaying image data of the interior of a tubular structure, wherein a structurally individualized simulation of the introduction of a wall support element into a section of a tubular structure is carried out with a simulation method as claimed in claim 1, and the simulation result is represented on the image display device together with the image data of the interior of the tubular structure.

17. A computer readable medium including program segments for, when executed on a computer device, causing the computer device to implement the method of claim 1.

18. A computer readable medium including program segments, which can be loaded directly into a memory of a computer unit for, when executed on a computer device, causing the computer device to implement the method of claim 1.

19. A simulation device for structurally individualized simulation of the introduction of a wall support element into a section of a tubular structure, comprising:
an image data interface to receive image data which include at least image data of the interior of the section of the tubular structure;
a position determination unit to determine a start point and an end point of the section of the tubular structure;
a lumen determination unit to determine a lumen of the section of the tubular structure between the start point and the end point on the basis of the image data;
a profile line determination unit to determine a profile line between the start point and the end point on the basis of the image data;
a structure model identification unit to identify an individual elastic structure model for the section of the tubular structure by adapting a tubular elastic initial model to the section of the tubular structure on the basis of the identified lumen and the profile line;
a wall support element model identification unit to provide a tubular elastic wall support element model which is positioned inside the individual structure model; and
an expansion unit to stepwise virtually expand the wall support element model, a check for collisions between the wall support element model and the individual structure model being carried out in each expansion step, and the wall support element model and the individual structure model being modified at least locally at the positions where a collision is identified, while taking into account the elasticity of the individual structure model.

20. A simulation device for structurally individualized simulation of the introduction of a wall support element into a section of a tubular structure, comprising:
image data interface means for receiving image data which include at least image data of the interior of the section of the tubular structure;

position determination means for determining a start point and an end point of the section of the tubular structure;

lumen determination means for determining a lumen of the section of the tubular structure between the start point and the end point on the basis of the image data;

profile line determination means for determining a profile line between the start point and the end point on the basis of the image data;

structure model identification means for identifying an individual elastic structure model for the section of the tubular structure by adapting a tubular elastic initial model to the section of the tubular structure on the basis of the identified lumen and the profile line;

wall support element model identification means for providing a tubular elastic wall support element model which is positioned inside the individual structure model; and expansion means for stepwise virtual expansion of the wall support element model, a check for collisions between the wall support element model and the individual structure model being carried out in each expansion step, and the wall support element model and the individual structure model being modified at least locally at the positions where a collision is identified, while taking into account the elasticity of the individual structure model.

* * * * *